US00RE37771E

(19) United States
(12) Reissued Patent
Waller et al.

(10) Patent Number: US RE37,771 E
(45) Date of Reissued Patent: Jun. 25, 2002

(54) PURIFICATION OF CINNAMOYL-C-GLYCOSIDE CHROMONE

(75) Inventors: Todd Waller, Harlingen, TX (US); Qi Jia, Arvada; Abeysinghe Padmapriya, Boulder, both of CO (US)

(73) Assignee: Univera Pharmaceuticals, Inc., Broomfield, CO (US)

(21) Appl. No.: 09/414,478

(22) Filed: Oct. 7, 1999

Related U.S. Patent Documents

Reissue of:
(64) Patent No.: 5,675,000
Issued: Oct. 7, 1997
Appl. No.: 08/621,178
Filed: Mar. 21, 1996

(51) Int. Cl.[7] ..... C07H 1/08
(52) U.S. Cl. ..... 536/128; 536/4.1; 536/124; 536/127
(58) Field of Search ..... 536/4.1, 124, 127, 536/128

(56) References Cited

U.S. PATENT DOCUMENTS 4,966,892 A 10/1990 McAnnalley ..... 514/54

OTHER PUBLICATIONS

Gramatica et al. (1982) Tetrahedron Letters 23:2423–2424.
Hart et al. (1988) J. of Ethnopharmacology 23:61–71.
Holdsworth (1972) *Chromones in Aloe Species, Part II—Aloesone*, PM 22(1):54–58.
Holdsworth (1972) *Chromones in Aloe Species, Part I—Aloesin*, PM 19(4):322–325.
Speranza et al. (1985) Phytochemistry 24:1571–1573.
Speranza et al. (1986) Phytochemistry 25:2219–2222.
Okamura et al., "Three Chromone Components from Aloe Vera Leaves", Phytochemistry, vol. 43, No. 2, pp. 495–498, 1996.*
Hutter et al., Journal of Natural Products, vol. 59; 541–543, (1996).*

* cited by examiner

*Primary Examiner*—Devesh Khare
(74) *Attorney, Agent, or Firm*—Swanson & Bratschun, L.L.C.

(57) ABSTRACT

The present invention provides a process for purifying the cinnamoyl-C-glycoside, [8-C-β-D-[2-O-(E)-cinnamoyl] glycopyranosyl-2- [(R)-2-hydroxy]propyl-7-methoxy-5-methyl-chromone.] *8-C-β-D-[2'-O- (E)-cinnamoyl] glycopyranosyl-2-[(S)-2-hydroxy]propyl-7-methoxy-5-methylchromone,* referred to herein as the "540 compound." In one embodiment of the present invention the 540 compound is purified by extraction from a decolorizing agent with an organic solvent. The extracted product can be purified by high pressure liquid chromatography. In a second embodiment crude 540 compound, which has not been treated with a decolorizing agent, is purified by passage over neutral alumina or sephadex.

19 Claims, 2 Drawing Sheets

PURIFICATION OF CINNAMOYL-C-GLYCOSIDE CHROMONE

Matter enclosed in heavy brackets [ ] appears in the original patent but forms no part of this reissue specification; matter printed in italics indicates the additions made by reissue.

FIELD OF INVENTION

The present invention relates generally to the purification of an anti-inflammatory and epithelial growth factor-inhibiting compound isolated from the Aloe barbadensis plant. Specifically, this invention describes the purification of the cinnamoyl-C-glycoside, [8-C-β-D-[2-O-(E)-cinnamoyl]glycopyranosyl-2-[(R)-2-hydroxy]propyl-7-methoxy-5-methyl-chromone.] *8-C-β-D-[2′-O-(E)-cinnamoyl]glycopyranosyl-2-[(S)-2-hydroxy]propyl-7-methoxy-5-methylchromone,* which has a molecular weight of 541 Daltons, and is referred to herein as the "540 compound."

BACKGROUND OF THE INVENTION

The aloe plant is an intricate plant which contains many biologically active substances. (Cohen et al. in Wound Healing/Biochemical and Clinical Aspects, 1st ed. W B Saunders, Philadelphia (1992)). Studies have shown that these biologically active substances are located in three separate sections of the aloe leaf—a clear gel fillet located in the center of the leaf, in the leaf rind or cortex of the aloe leaf and in a yellow fluid contained in the pericyclic cells of the vascular bundles, located between the leaf rind and the internal gel fillet. Historically, aloe products have been used in dermatological applications for the treatment of burns, sores and other wounds. These uses have stimulated a great deal of research on identifying compounds from aloe plants that have clinical activity, especially anti-inflammatory activity. (See, e.g., Grindlay and Reynolds (1986) J. of Ethnopharmacology 16:117–151; Hart et al. (1988) J. of Ethnopharmacology 23:61–71).

A variety of methods are currently used for the isolation and purification of products from the aloe plant. In conventional prior art methods the entire aloe leaf is crushed to produce an aloe vera juice, which is then purified by various steps of filtration and stabilization, to yield a purified mixture of compounds. See, McAnnalley, U.S. Pat. No. 4,966,892, entitled Processes for Preparation of Aloe Products, Products Produced Thereby and Composition Thereof, for a detailed explanation of conventional prior art methods. As explained by McAnnalley, conventional methods fail to take into account that the three separate segments of the aloe leaf—the gel fillet, leaf rind and yellow fluid or latex—have varied compositions containing compounds which may be inconsistent with the intended use of the final composition. McAnnalley describes an improved method of purification wherein the various segments of the aloe leaf are first separated prior to processing.

In other more recent methods, the purification of individual compounds from various aloe plants is described. For example, Holdsworth describes a purification scheme for two Aloe chromones—Aloesin and Aloesone—using chromatography followed by counter current extraction. (Holdsworth (1972) Chromones in Aloe Species, Part I-Aloesin. PM 19(4): 322–325; Holdsworth (1972) Chromones in Aloe Species, Part II Aloesone, PM 22(1): 54–58. Speranza and coworkers describe the purification and identification of a number of Aloe chromones using a combination of droplet counter current chromatography and flash chromatography (Speranza et al. (1986) Phytochemistry 25: 2219–2222); and a combination of flash chromatography and high pressure liquid chromatography (HPLC) (Speranza et al. (1985) Phytochemistry 24:1571–1573; Gramatica et al. (1982) Tetrahedron Letters 23:2423–2424).

In one process for isolating the 540 compound, gel or rind slurry of the Aloe barbadensis plant is dialyzed, suspended in ethanol, agitated and centrifuged. (U.S. application Ser. No. 08/391,139, entitled Cinnamoyl-C-Glycoside Chromone Isolated from Aloe barbadensis, filed Feb. 21, 1995, which is incorporated herein by reference). The ethanol is stripped from the supernatant, and the resultant product extracted with a mixture of chloroform and water. The chloroform phase is evaporated and lyophilized, and then taken up in ethanol. Use of this process indicated retained activity, however, the process failed to yield compound 540 of sufficient purity.

Neither this process nor any of the other reported prior art processes for purification of aloe compounds, provide a commercially viable process for the purification of compound 540.

SUMMARY OF THE INVENTION

The present invention includes a process for isolating and purifying the cinnamoyl-C-glycoside, [8-C-β-D-[2-O-(E)-cinnamoyl]glycopyranosyl-2-[(R)-2-hydroxy]propyl-7-methoxy-5-methyl-chromone] *8-C-β-D-[2′-O-(E)-cinnamoyl]glycopyranosyl-2-[(S)-2-hydroxy]propyl-7-methoxy-5-methylchromone* from the aloe plant. In one embodiment of the present invention, the method comprises: contacting a decolorizing agent, which has been obtained from the processing of a slurry of an aloe leaf extract, with an organic solvent to extract the absorbed 540 compound from the decolorizing agent into the organic solvent, thereby forming a mixture of decolorizing agent and organic solvent containing the 540 compound; separating the decolorizing agent from the organic solvent to yield a solution highly enriched in compound 540. Optionally, the 540 compound is further purified using reversed phase high pressure liquid chromatography (HPLC) or by conventional chromatographic methods, such as column chromatography.

In a second embodiment of the present invention crude extracts of the 540 compound, isolated from the leaf rind of the aloe plant, are purified by column chromatography. This method of purification comprises: purifying the crude methanol or ethanol extract by passage over neutral alumina or sephadex.

The present invention provides a commercially viable process for the purification of compound 540 having desirable physiological activity.

DETAILED DESCRIPTION OF THE INVENTION

Figure 1:
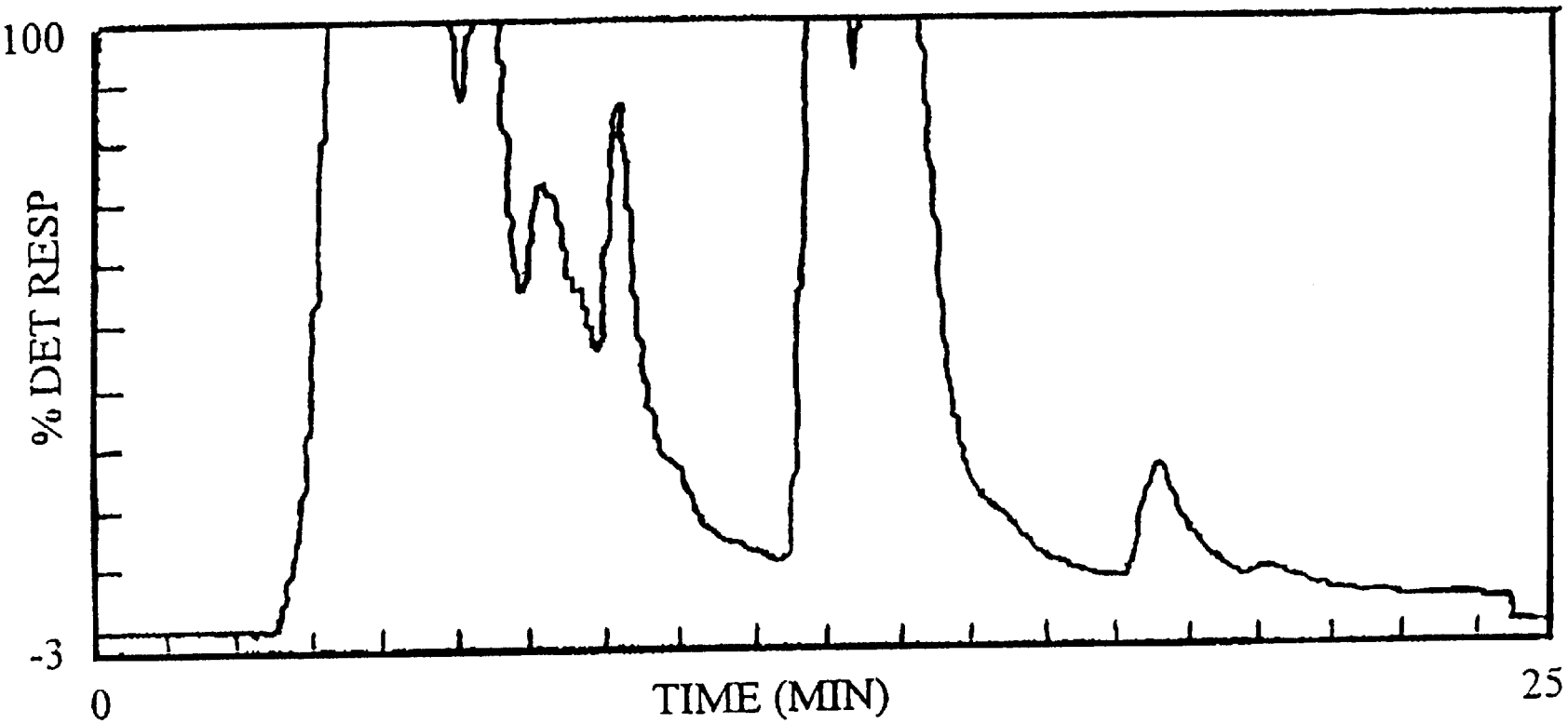
FIG. 1 depicts a representative HPLC spectrum showing a peak characteristic of compound 540 at 14.79 minutes (eluted with 55% $CH_3OH$/45% $H_2O$, monitored at 205 nm).

The present invention includes a novel process for the purification of the cinnamoyl-C-glycoside, [8-C-β-D-[2-O-(E)-cinnamoyl]glycopyranosyl-2-[(R)-2-hydroxy]propyl-7-methoxy-5-methyl-chromone] *8-C-β-D-[2′-O-(E)-*

*cinnamoyl*]*glycopyranosyl-2-*[(*S*)*-2-hydroxy*]*propyl-7-methoxy-5-methylchromone* (the "540 compound"). This compound is present primarily in the leaf rind of the Aloe barbadensis plant and has the following chemical structure:

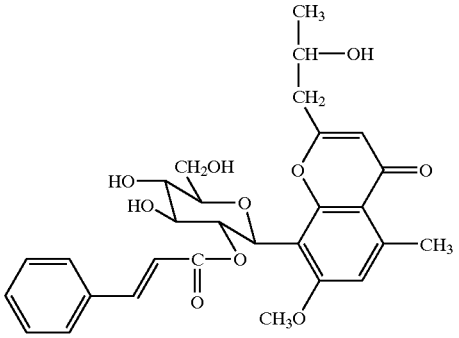

The 540 compound exhibits potent anti-inflammatory activity as measured by in vivo assays. This compound has also been shown to inhibit EGF-induced DNA synthesis in in vitro testing in epithelial cell lines. The isolation and structural determination of the 540 compound and its activity are described in greater detail in related U.S. application Ser. No. 08/391,139, entitled Cinnamoyl-C-Glycoside Chromone Isolated from Aloe barbadensis, filed Feb. 21, 1995, which is incorporated herein by reference.

Several commercial processes employed in the processing of slurries from aloe leaf extracts utilize activated carbon (also referred to as activated charcoal) to improve the color of the extracts. Treatment with activated carbon is particularly common with so-called "whole-leaf processing", wherein the entire leaf is ground and processed. A series of experiments on aloe extracts, which had been isolated from the Aloe barbadensis plant, followed by treatment with activated carbon led to the discovery that certain activity associated with the 540 compound was not present in the extracts after treatment with the activated carbon. This led to the discovery that the 540 compound is absorbed by activated carbon. (See, U.S. application Ser. No. 08/391,139, entitled Cinnamoyl-C-Glycoside Chromone Isolated from Aloe barbadensis, filed Feb. 21, 1995). A key feature in the method of the first embodiment of the present invention is the extraction of compound 540 from decolorizing agents, such as activated charcoal, using an organic solvent, preferably an alkyl alcohol, such as ethanol and methanol or mixtures containing methanol or ethanol. A particularly attractive aspect of this procedure is the use of spent (waste) activated charcoal or decolorizing agent from commercial processes as the starting material.

In a second embodiment of the present invention crude aloe extract, isolated from the leaf rind of the aloe plant is purified by column chromatography without first being treated with a decolorizing agent. This method cuts out a step in the processing of the extracts and provides a fast and simple method of purification, which is ideally suited for large scale production.

In the first embodiment of the present invention, described in Example 1, a decolorizing agent, isolated from the processing of a slurry prepared from aloe leaf extracts, is treated with an organic solvent to extract the absorbed 540 compound. In a preferred embodiment the slurry from which the decolorizing agent is isolated is prepared from the whole leaf or the leaf rind of the Aloe barbadensis plant. Because the majority of the 540 compound is present in the leaf rind or latex, in the most preferred embodiment the slurry is prepared from the leaf rind or latex. In the preferred embodiment the decolorizing agent is activated charcoal, however any of the synthetic resins which are currently used as decolorizing agents, such as, AMBERLITE® resin (e.g. XAD-2 resin) can also be used.

The organic solvent used to extract the 540 compound from the decolorizing agent can be selected from an alkyl alcohol, such as methanol or ethanol, or can be selected from other organic solvents or mixtures containing MeOH or EtOH typically used in extraction processes, such as acetone. Because the decolorizing agent is wet water soluble organic solvents are preferred. The use of water insoluble solvents, such as methylene chloride, requires that the decolorizing agent be dried prior to extraction, which becomes extremely costly on a large scale. Additionally, methanol and ethanol were found to be more efficient at extracting the 540 compound from the decolorizing agent than acetone (as determined by analytical HPLC) (See Examples 1 and 3). In the most preferred embodiment, therefore, the organic solvent is an alkyl alcohol selected from the group consisting of methanol or ethanol or mixtures containing MeOH or EtOH. The organic solvent acts both to extract the 540 compound from the decolorizing agent and to regenerate the decolorizing agent for further use in the processing of aloe leaf extracts.

The extraction can be conducted within a temperature range of ambient temperature to the boiling point of the solvent being used. The preferred temperature range is 40°–60° C.

In another embodiment of the invention, described in Examples 2 and 3, the organic extract is concentrated and the residue is dissolved in water. The aqueous solution is then extracted with an organic solvent. This step serves to remove a number of impurities, particularly the anthraquinones, that are present in the crude extract and remain in the aqueous layer. In the preferred embodiment the organic solvent is selected from the group consisting of: n-butanol, ethyl acetate or methylene chloride. In the most preferred embodiment methylene chloride is used. Following extraction from water, the 540 compound is approximately 30–35% pure. Finally, preparative high pressure liquid chromatography (HPLC) may be used to further purify the 540 compound. The 540 compound is isolated in greater than 95% purity by collecting the appropriate elution volume from HPLC.

The present invention therefore includes a method for purifying the 540 compound isolated from either whole leaf aloe extract or leaf rind extract comprising the steps of: (1) contacting a decolorizing agent, which has been isolated from the processing of aloe leaf extracts, with an organic solvent to extract the 540 compound from the decolorizing agent into the organic solvent, thereby forming a mixture of decolorizing agent and organic solvent containing the 540 compound; and (2) subsequently filtering the mixture so as to separate the decolorizing agent from the organic solvent.

Optionally, the method comprises an additional step (3) wherein the 540 compound isolated from step (2) is concentrated, dissolved in water and further extracted with an organic solvent, such as, n-butanol, ethyl acetate or methylene chloride to remove any water soluble impurities that may be present.

Alternatively, after step (2) or after step (3), the resultant organic phase can be concentrated and further purified by preparatory HPLC.

In a second embodiment of the present invention crude aloe extract isolated from the leaf rind is purified by passage over Sephadex® (Example 6) or neutral alumina (Example 5) without first being treated with a decolorizing agent. In the preferred embodiment the 540 compound is further purified using alumina. Neutral alumina removes all of the acidic impurities from the crude product, including any phenolic compounds and yields a product that is approximately 64% pure. Additionally, the procedure is simple and fast and ideally suited for large scale production.

The following examples are provided for illustrative purposes only and are not intended to limit the scope of the invention.

EXAMPLE 1

Extraction of the 540 Compound from Activated Carbon using Methanol and Acetone (room temperature).

Five hundred grams of freeze-dried, spent activated carbon from whole leaf production was placed in a 2 liter beaker. One and one half liters of methanol was added and the slurry was stored at room temperature for 2 hours. After 2 hours, the slurry was filtered through 0.5 micron cellulose filter paper. The filtrate was stripped of methanol under vacuum and the residue subjected to HPLC analysis. The procedure was then repeated using acetone as the solvent.

Analytical HPLC Analysis

Column: ODS-1, 4 mm×250 mm, 5 $\mu$ particle size

Temperature: Ambient

Mobile Phase: 55% methanol/45% water

Flow Rate: 0.70 ml/min

Detector Wavelength: 205 nm

Injection Volume: 10–20 $\mu$l

Sensitivity: 0.20 AUFS

Retention Time: Approximately 16–17 min.

HPLC analysis shows that methanol is more effective at extracting the 540 compound from the decolorizing agent than acetone. An illustrative HFLC spectrum of the 540 compound is depicted in FIG. 1.

EXAMPLE 2

Isolation of the 540 Compound from Activated carbon 40° C.

Five hundred grams of dried, spent activated carbon from whole leaf processing was placed in a 4 liter beaker. One and one-half liters of methanol was added to the beaker and the slurry was stirred for 1 hour at 40° C. The slurry was then filtered through 0.5 micron filter paper, using 250 ml of fresh methanol as a wash. The methanol was evaporated under vacuum and the residue was dissolved in 500 ml of distilled water. The aqueous solution was then extracted with methylene chloride (3×100 ml). The methylene chloride extracts were combined and evaporated and 20 ml of methanol was added to the residue and the slurry was centrifuged. The above procedure was then repeated using acetone in place of methanol.

Analytical HPLC analysis of both extracts (using the conditions set forth in Example 1) indicated that a number of the impurities, specifically the anthraquinones, had been removed from the crude extract. The product isolated was approximately 30–35% pure as determined by HPLC.

Both pools were combined and further purified by preparative HPLC to yield the 540 compound in greater than 95% purity.

Preparative HPLC.

Column: ODS-1, 22 mm×250 mm, 10 1 $\mu$ particle size

Mobile Phase: 45% methanol/55% water

Temperature: Ambient

Flow Rate: 15 ml/min

Detector Wavelength: 205 nm

Sensitivity: 0.05 AUFS

Product eluted between 20–24 minutes. The solvent was evaporated and the residue lyophilized. Structural analysis was then performed on the lyophilized product which confirmed the characterization of compound 540. The structural elucidation was accomplished by use of nuclear magnetic resonance ($^1$H) spectroscopy and mass spectrometry, evaluation of ultraviolet absorbance, melting point and thin-layer chromatographic behavior. The results were as follows:

Analytical data and methodology:

Melting Point: sublimes>90° C.

Thin-layer chromatography:

TLC plate: Silica

Solvent system: ethyl acetate/methanol/water (100:13:3, v/v/v)

$R_f$: 0.69

UV Spectrum

Solvent: $CH_3OH$ $\lambda_{max}$ (log e): 246 nm (4.22), 254 nm (4.27), 284 nm (4.36)

Proton NMR analysis:

Instrument: General Electric model QE 300 spectrometer

Frequency: 300 mHz

Solvent: $CD_3OD$

Reference: $CH_3OH$, 330 ppm

Spectral data: 1.30 (3H, d, 6 Hz) (2-γ-methyl); 2.74 (3H, s) (5-methyl); 2.82 (2H, dd, 14 Hz, 6.5 Hz) (2-α-methylene); 3.42–3.50 (1H, m) (5'-H); 3.61 (1H, dd, 10 Hz) (4'-H); 3.70–3.80 (2H, m) (3'6'a-H); 3.89 (3H, s) (7-methoxy); 4.00 (1H, m) (6'b-H); 4.37 (1H, m) (2-β-carbionl); 5.21 (1H, d, 10 Hz) (1'-H); 5.73 (1H, dd, 10 Hz) (2'-H); 6.13, (1H, s) (3-H); 6.27 (1H, d, 16 Hz) (cinnamoyl β-H); 6.81 (1H, s) (6-H); 7.37 (2H, m) (cinnamoyl m-H); 7.45 (1H, d, 16 Hz) (cinnamoyl β-H); 7.50 (3H, m) (cinnamoyl o-, p-H)

Mass spectral analysis:

Instrument Finnigan MAT 4615 quadrupole mass spectrometer

Ionization: electron impact (70 eV)

Source temperature: 160° C.

Sample introduction: direct insertion probe

Sample heating: ballistic; peak evaporation at approximately 250° C.

Spectral data (relative to intensity in parenthesis): m/z 540 (12), $[M]^+$; m/z 522 (5), $[M\text{-}H_2O]^+$ $([M-18]^+)$; m/z 496 (4), $[M—CH^3CHO]^{+(*)}$ $([M\text{-}44]^{+)}$; $^{m/z}$410 (16), $[M\text{-cinnamoyl}]^{+()}$ $([M\text{-}130]^+)$; m/z 392 (10), $[M\text{-}(130+18)]^+$; m/z 376 (4), $[M\text{-}(18+\text{cinnamate})]^{+()}$ $([M\text{-}(18+146]^+$; m/z 366 (8), $[M\text{-}(130+44)]^+$; m/z 343 (18), $[M\text{-}(18+147+33)]^{+(*)}$; m/z 277 (50), $[M\text{-}(130+133)]^{+()}$; m/z 259 (100), $[M\text{-}(130+18+133)]^+$; m/z 233 (92), $[M\text{-}(130+44+133)]^+$; m/z 193 (73), $[M\text{-}(130+84^{(***)}+133)]^+$; m/z 131 (40), $[\text{cinnamoyl}]^+$; m/z 103 (33), $[C_6H_5CHCH]^+$

*alpha-cleavage of the 2-hydroxypropyl side chain

**involves hydrogen transfer

***tentative assignment

****133 represents C2–C6 of the C-glycoside

*****retro-Diels Alder fragmentation that includes the hydroxypropyl side chain

EXAMPLE 3

Extraction of the Crude 540 Compound from Water.

One hundred grams of methanol eluate from spent activated carbon from whole leaf processing, as described in Example 2, was dissolved in 1500 ml of distilled water. The solution was divided into three equal portions, each of which was extracted with one the following solvents (3×10 ml): ethyl acetate, n-butanol and methylene chloride. The organic extracts were analyzed by HPLC, which indicated that methylene chloride was the most effective of the three solvents for extraction of the 540 compound from water.

EXAMPLE 4

Extraction of the 540 Compound from Activated Carbon using Ethanol and Acetone (40° C.).

Fifty grams of dried spent activated carbon from whole leaf processing was placed in a 500 ml beaker. Acetone (200 ml) was added and the mixture was stirred at 40° C. for one hour. The resultant slurry was filtered through 0.5 micron cellulose filter paper and the cake washed with 100 ml of fresh acetone. The acetone was stripped and the sample freeze-dried. This procedure was repeated from the beginning with another 50 grams of spent activated carbon using ethanol. The yield from the acetone elution was 1.34 grams and the yield from the ethanol elution was 5.24 grams.

EXAMPLE 5

Purification of the 540 Compound using Alumina.

Neutral alumina oxide (A1203) (600 g), purchased from Sigma (Type WN-3), was placed in a Büchner funnel. A methanolic solution of compound 540 from the rind, which had not been treated with a decolorizing agent (400 ml of a 14.68% solution as measured by HPLC) was applied to the alumina and eluted with 2 liters of methanol, which was collected as follows:

| | Elution Volume | Dry Weight (g) | Purity of Compound 540 (%) |
|---|---|---|---|
| Fraction 1 | 0–50 ml | 0.350 | 100 |
| Fraction 2 | 51–100 ml | 0.461 | 96.77 |
| Fraction 3 | 101–1000 ml | 7.6 | 64.86 |
| Fraction 4 | 1001–2000 ml | 0 | |

Figure 2:
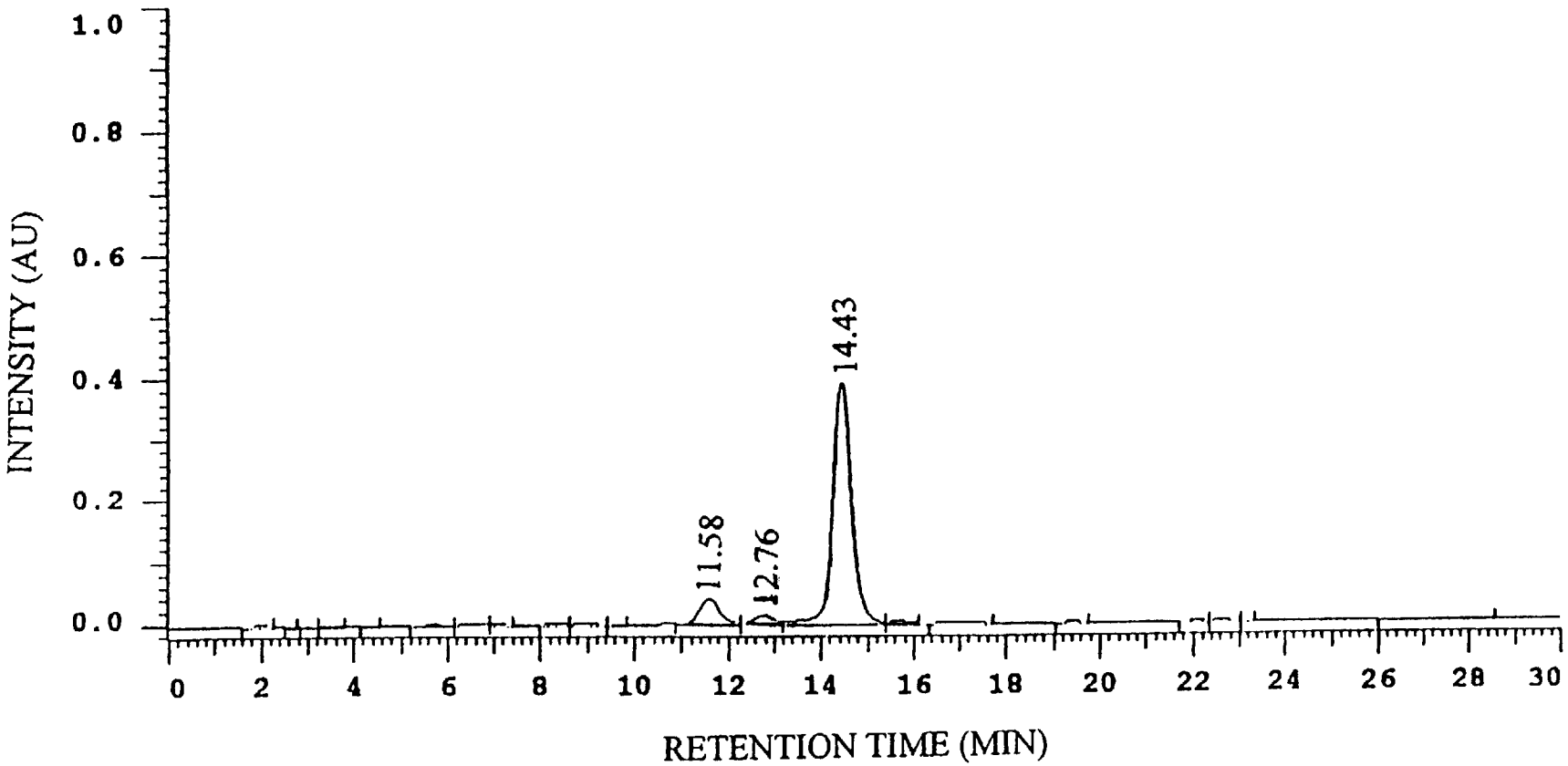
FIG. 2 shows high purity Compound 540 detected by HPLC.

Purity was measured by HPLC analysis of the eluent. (See FIG. 2). HPLC operating conditions were the same as described in Example 1, except the detector wavelength was 297 nm and flowrate was 1.0 ml/min.

EXAMPLE 6

Purification of the 540 Compound on a Sephadex Column.

Sephadex (200 g, LH-20, 30-100 μm mesh, purchased from Pharmacia Biotech Co., California) was packed into a 5.0×40 cm chromatography column. A methanolic solution of compound 540 (10 g in 25 ml methanol) was applied to the column and eluted with a 1:1 solution of methanol and water at a flow rate of 5–6 ml/min. (The 540 compound used in this example was obtained by ethanol extraction of activated carbon and was approximately 16% pure as determined by analytical HPLC). After 150 ml of solvent had eluted, 50 ml fractions were collected and analyzed by HPLC. Fractions 7–11 were combined, concentrated and lyophilized to yield 633 mg of compound 540 (35.8% pure)

What is claimed is:

1. A method for purifying [8-C-β-D-[2-O-(E)-cinnamoyl] glycopyranosyl-2-[(R)-2-hydroxy]propyl-7-methoxy-5-methyl-chromone] *8-C-β-D-[2′-O-(E)-cinnamoyl] glycopyranosyl-2-[(S)-2-hydroxy]propyl-7-methoxy-5-methylchromone* (the "540 compound"), comprising the steps of:

(a) contacting a decolorizing agent, which has been obtained from the processing of a slurry of an aloe leaf extract, with an organic solvent to extract the absorbed 540 compound from the decolorizing agent into the organic solvent, thereby forming a mixture of decolorizing agent and organic solvent containing the 540 compound; and (b) separating the decolorizing agent from the organic solvent to yield a solution highly enriched in compound 540.

2. The method of claim 1, further comprising the step of:

(c) purifying the solution obtained in step (b) by high pressure liquid chromatography (HPLC).

3. The method of claim 1 wherein the aloe leaf exact is obtained from the Aloe barbadensis plant.

4. The method of claim 1 wherein the aloe leaf extract is obtained from the whole leaf of the aloe plant.

5. The method of claim 1 wherein the aloe leaf extract is obtained from the leaf rind of the aloe plant.

6. The method of claim 1 wherein the decolorizing agent is selected from the group consisting of activated carbon or a synthetic resin.

7. The method of claim 6 wherein the synthetic resin is an AMBERLITE® resin.

8. The method of claim 7 wherein said AMBERLITE® resin is XAD-2.

9. The method of claim 1 wherein the organic solvent is an alkyl alcohol, selected from the group consisting of methanol, ethanol or mixtures derived from ethanol or methanol.

10. The method of claim 1 wherein the decolorizing agent is contacted with the organic solvent between ambient temperature and the boiling point of the organic solvent.

11. The method of claim 10 wherein the decolorizing agent is contacted with the organic solvent within a temperature range of 40° C.–60° C.

12. The method of claim 1 further comprising the steps of:

(c) concentrating the solution obtained in step (b);

(d) adding water to the concentrated residue to form an aqueous solution; and (e) extracting the aqueous solution with an organic solvent.

13. The method of claim 12 wherein the organic solvent is selected from the group consisting of butanol, ethyl acetate or methylene chloride.

14. A method for purifying compound 540 isolated from the aloe plant comprising the steps of:

(a) applying a solution of crude aloe extract to a pad of neutral alumina; and (b) eluting the extract with an organic solvent.

15. The method of claim 14 wherein the crude aloe extract is isolated from the leaf rind of the Aloe barbadensis plant.

16. The method of claim 14 wherein the organic solvent is selected from the group consisting of methanol and ethanol.

17. A method for purifying compound 540 isolated from the aloe plant comprising the steps of:

(a) applying a solution of crude aloe extract to a Sephadex, column; and (b) eluting the extract with an organic solvent.

18. The method of claim 17 wherein the crude aloe extract is isolated from the leaf rind of the Aloe barbadensis plant.

19. The method of claim 17 wherein the organic solvent is selected from the group consisting of methanol or ethanol.

* * * * *